United States Patent [19]
Hsieh et al.

[11] Patent Number: 6,061,419
[45] Date of Patent: May 9, 2000

[54] METHODS AND APPARATUS FOR NOISE COMPENSATION IN AN IMAGING SYSTEM

[75] Inventors: Jiang Hsieh; Thomas L. Toth, both of Brookfield, Wis.

[73] Assignee: General Electric Company, Milwaukee, Wis.

[21] Appl. No.: 09/139,833

[22] Filed: Aug. 25, 1998

[51] Int. Cl.$^7$ ........................................................ A61B 6/03
[52] U.S. Cl. .................................................. 378/4; 378/901
[58] Field of Search .................................. 378/4, 15, 901

[56] References Cited

U.S. PATENT DOCUMENTS 5,491,735  2/1996  Hsieh .......................................... 378/15

*Primary Examiner*—David V. Bruce
*Attorney, Agent, or Firm*—Armstrong, Teasdale; Christian G. Cabou; Phyllis Y. Price

[57] ABSTRACT

Methods and apparatus for performing channel dependent and gain dependent smoothing filter (across channels) to compensate for noise in a multislice imaging system are described. The smoothing mainly affects the radial resolution. The filter can be combined with the matrix deconvolution filter typically used in multi-slice scanners. The filter is channel and DAS gain dependent and provides that an image generated from data collected in a multi-slice scan has about the same image quality, e.g., noise reduction, as images generated by other types of scanners.

16 Claims, 3 Drawing Sheets

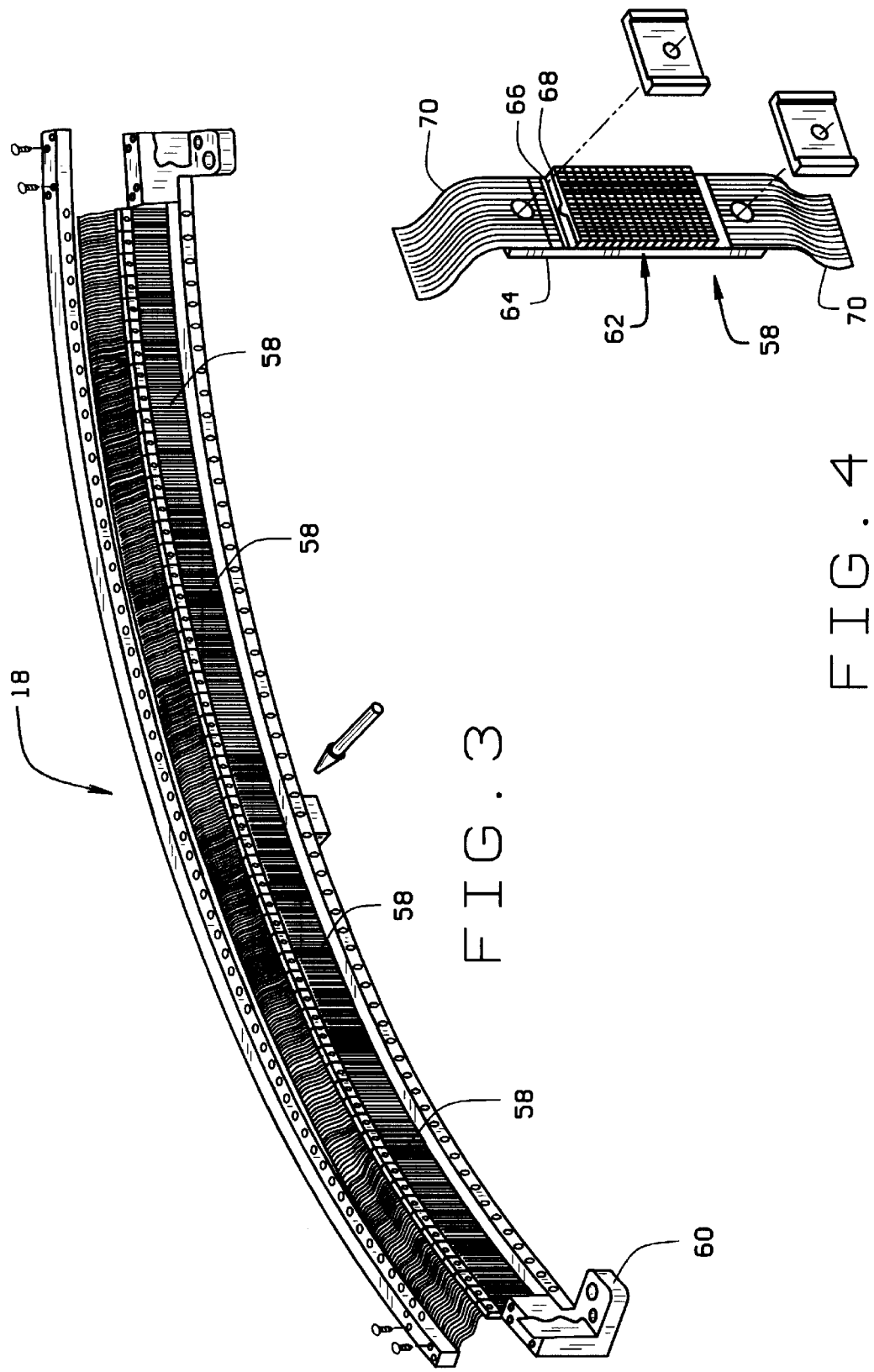

METHODS AND APPARATUS FOR NOISE COMPENSATION IN AN IMAGING SYSTEM

BACKGROUND OF THE INVENTION

This invention relates generally to imaging and, more particularly, to generating images from projection data collected in a multislice imaging system. In at least one known imaging system generally referred to as a computed tomography (CT) system, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a post patient collimator for collimating scattered x-ray beams received at the detector. A scintillator is located adjacent the post patient collimator, and photodiodes are positioned adjacent the scintillator.

Multislice CT systems are used to obtain data for an increased number of slices during a scan. Known multislice systems typically include detectors generally known as 3-D detectors. With such 3-D detectors, a plurality of detector elements form separate channels arranged in columns and rows. Each row of detectors forms a separate slice. For example, a two slice detector has two rows of detector elements, and a four slice detector has four rows of detector elements. During a multislice scan, multiple rows of detector cells are simultaneously impinged by the x-ray beam, and therefore data for several slices is obtained.

Images generated by multi-slice scanners may, however, appear to be somewhat noisier than images produced by other known types of scanners, such as CT/i scanners, at the recommended x-ray tube current reduction factor. For example, one embodiment of a multislice scanner uses a shorter geometry which increases image noise away from the center of the image compared to other known longer geometry scanner. More particularly, and as a result of the geometry change and the fan beam reconstruction in the multislice system, to reduce the concentric force on the x-ray tube, the x-ray tube to iso-center distance needs to be reduced. Consequently, the magnification factor for such scanner increases, the scaling factor used in the fan beam backprojection increases, and the noise in the reconstructed image also increases. It would be desirable to provide that an image generated from data collected in a short geometry multislice scan has about the same image quality, e.g., noise reduction, as images generated by other types of scanners.

BRIEF SUMMARY OF THE INVENTION

These and other objects may be attained by a multi-slice CT system which, in one embodiment, includes a channel dependent and DAS gain and noise dependent smoothing filter (across channels) to compensate for the noise increase. The smoothing mainly affects the radial resolution. The filter can be combined with the matrix deconvolution filter typically used in multi-slice scanners for off-focal radition compensation to provide a filter described as $$H(\gamma, k) = f(\gamma, k, g) \otimes D(\gamma, k) \quad (1)$$

where H is the resulting composite filter that replaces the matrix deconvolution kernel, D, and $f$ is the channel and DAS gain dependent smoothing filter convolved with the matrix deconvolution kernel D to produce the new kernel H. Also, $\gamma$ is the channel, g is the gain, and k represents the detector row number.

The above described filter is channel and DAS gain dependent and provides that an image generated from data collected in a multi-slice scan has about the same image quality, e.g., noise reduction, as images generated by other types of scanners.

BRIEF DESCRIPTION OF THE DRAWINGS

FIG. 3 is a perspective view of a CT system detector array.

FIG. 4 is a perspective view of a detector module.

DETAILED DESCRIPTION OF THE INVENTION

Set forth below is a description of an exemplary multislice CT system in accordance with one embodiment of the present invention. Although one embodiment of the system is described in detail below, it should be understood that many alternative embodiments of the inventions are possible. For example, although one particular detector is described, the present invention could be utilized in connection with other detectors, and the present invention is not limited to practice with any one particular type of multislice or single slice detector. Specifically, the detector described below includes a plurality of modules and each module includes a plurality of detector cells. Rather than the specific detector described below, a detector which has multiple modules with multiple elements along the x-axis and/or z-axis joined together in either direction to acquire multi-slice scan data simultaneously, can be utilized. Generally, the system is operable in a multislice mode to collect 1 or more slices of data. Axial and helical scans can be performed with the system, and cross section images of a scanned object can be processed, reconstructed, displayed and/or archived.

Figure 1:
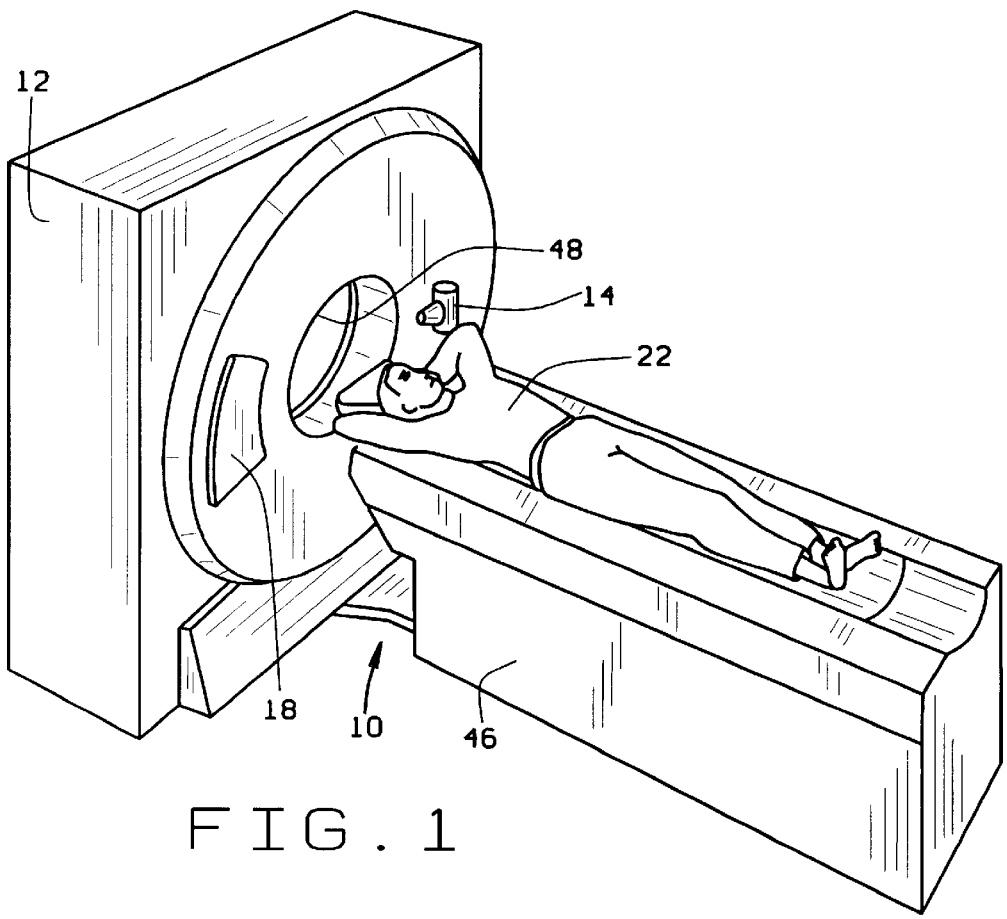
FIG. 1 is a pictorial view of a CT imaging system.
Figure 2:
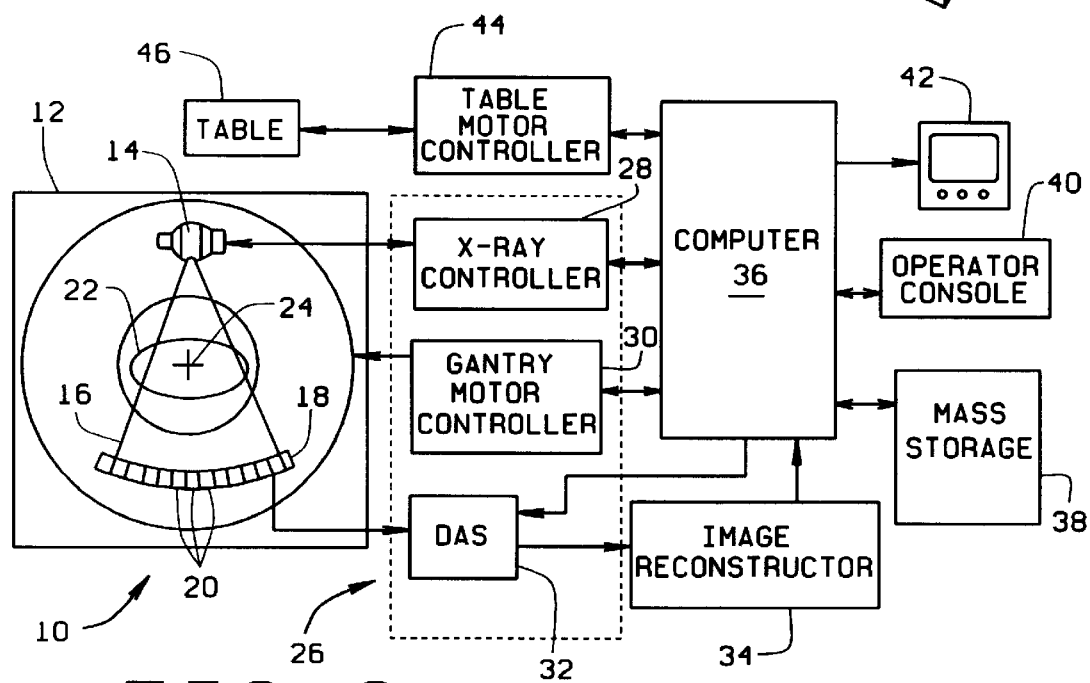
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 8 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10.

Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives and supplies signals via a user interface, or graphical user interface (GUI). Specifically, computer receives commands and scanning parameters from an operator via console 40 that has a keyboard and a mouse (not shown). An associated cathode ray tube display 42 allows the operator to observe the reconstructed image and other data from computer 36. The operator supplied commands and parameters are used by computer 36 to provide control signals and information to x-ray controller 28, gantry motor controller 30, DAS 32, and table motor controller 44.

As shown in FIGS. 3 and 4, detector array 18 includes a plurality of detector modules 58. Each detector module 58 is secured to a detector housing 60. Each module 58 includes a multidimensional scintillator array 62 and a high density semiconductor array (not visible). A post patient collimator (not shown) is positioned over and adjacent scintillator array 62 to collimate x-ray beams before such beams impinge upon scintillator array 62. Scintillator array 62 includes a plurality of scintillation elements arranged in an array, and the semiconductor array includes a plurality of photodiodes (not visible) arranged in an identical array. The photodiodes are deposited, or formed on a substrate 64, and scintillator array 62 is positioned over and secured to substrate 64.

Detector module 58 also includes a switch apparatus 66 electrically coupled to a decoder 68. Switch apparatus 66 is a multidimensional semiconductor switch array of similar size as the photodiode array. In one embodiment, switch apparatus 66 includes an array of field effect transistors (not shown) with each field effect transistor (FET) having an input, an output, and a control line (not shown). Switch apparatus 66 is coupled between the photodiode array and DAS 32. Particularly, each switch apparatus FET input is electrically connected to a photodiode array output and each switch apparatus FET output is electrically connected to DAS 32, for example, using flexible electrical cable 70.

Decoder 68 controls the operation of switch apparatus 66 to enable, disable, or combine the outputs of the photodiode array in accordance with a desired number of slices and slice resolutions for each slice. Decoder 68, in one embodiment, is a decoder chip or a FET controller as known in the art. Decoder 68 includes a plurality of output and control lines coupled to switch apparatus 66 and computer 36. Particularly, the decoder outputs are electrically connected to the switch apparatus control lines to enable switch apparatus 66 to transmit the proper data from the switch apparatus inputs to the switch apparatus outputs. The decoder control lines are electrically connected to the switch apparatus control lines and determine which of the decoder outputs will be enabled. Utilizing decoder 68, specific FETs within switch apparatus 66 are enabled, disable, or combined so that specific outputs of the photodiode array are electrically connected to CT system DAS 32. In one embodiment defined as a 16 slice mode, decoder 68 enables switch apparatus 66 so that all rows of the photodiode array are electrically connected to DAS 32, resulting in 16 separate, simultaneous slices of data being sent to DAS 32. Of course, many other slice combinations are possible.

In one specific embodiment, detector 18 includes fifty-seven detector modules 58. The semiconductor array and scintillator array 62 each have an array size of 16×16. As a result, detector 18 has 16 rows and 912 columns (16×57 modules), which enables 16 simultaneous slices of data to be collected with each rotation of gantry 12. Of course, the present invention is not limited to any specific array size, and it is contemplated that the array can be larger or smaller depending upon the specific operator needs. Also, detector 18 may be operated in many different slice thickness and number modes, e.g., one, two, and four slice modes. For example, the FETs can be configured in the four slice mode, so that data is collected for four slices from one or more rows of the photodiode array. Depending upon the specific configuration of the FETs as defined by decoder control lines, various combinations of outputs of the photodiode array can be enabled, disabled, or combined so that the slice thickness may, for example, be 1.25 mm, 2.5 mm, 3.75 mm, or 5 mm. Additional examples include a single slice mode including one slice with slices ranging from 1.25 mm thick to 20 mm thick, and a two slice mode including two slices with slices ranging from 1.25 mm thick to 10 mm thick. Additional modes beyond those described are possible.

Figure 5:
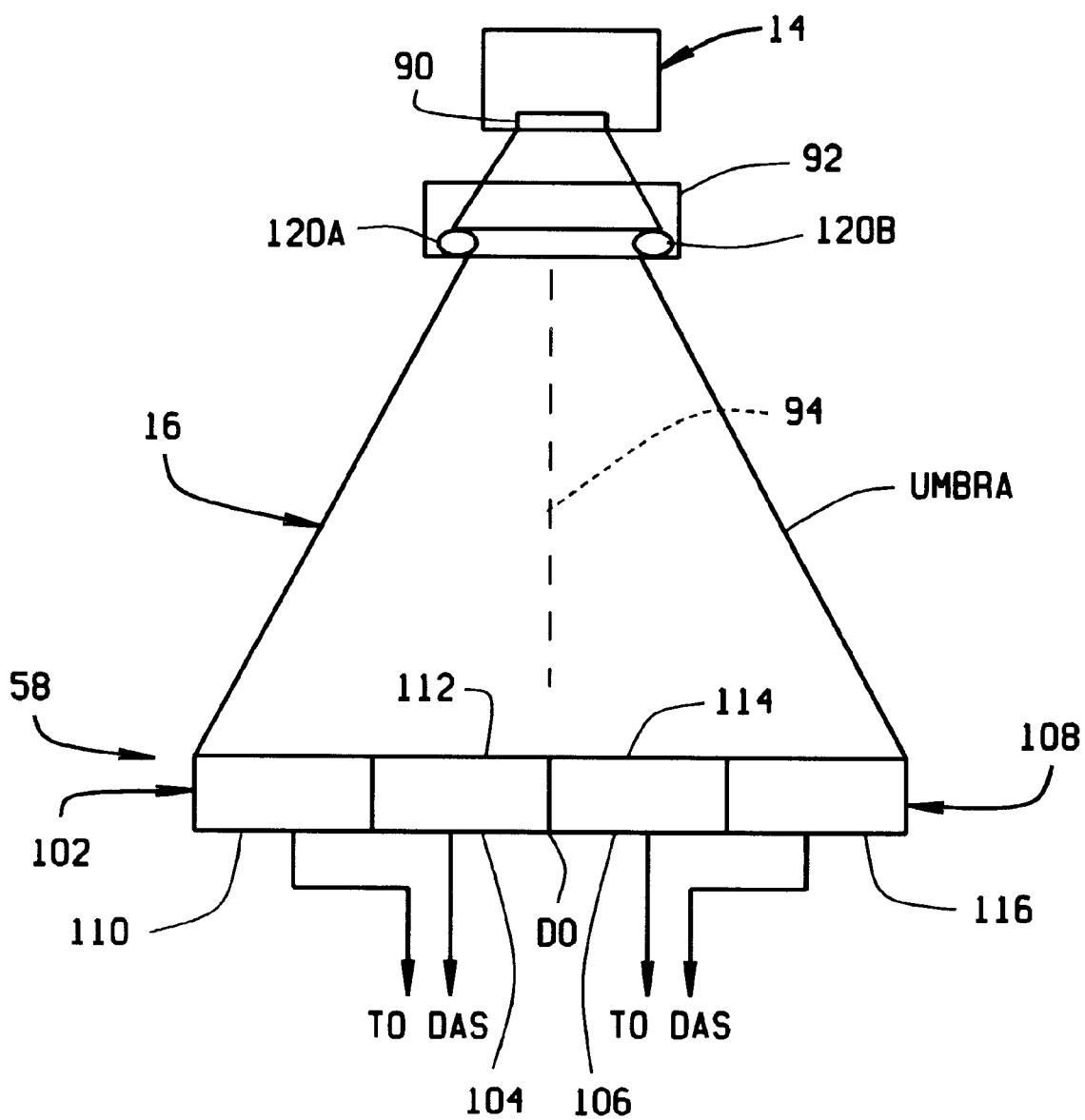
FIG. 5 is a schematic view of the CT imaging system shown in FIG. 1.

FIG. 5 is a simplified schematic view of a "four (or quad) slice" system in that four rows 102, 104, 106 and 108 of detector cells are utilized to obtain projection data. Detector cells 110, 112, 114 and 116 form rows 102, 103, 106 and 108. Each detector cell 110, 112, 114, and 116 illustrated in FIG. 5 may actually be composed of a number of cells (e.g., four) ganged together to produce one output which is supplied to DAS 32.

In one embodiment, collimator 92 includes eccentric cams 120A and 120B. The position of cams 120A and 120B are controlled by x-ray controller 28. Cams 120A and 120B are positioned on opposing sides of fan beam plane 94 and may be independently adjusted with respect to the spacing between cams 120A and 120B and their location relative to fan beam plane 94. Cams 120A and 120B may be positioned with a single cam drive, or alternatively, each cam may be positioned with a separate cam drive, for example a motor. Cams 120A and 120B are fabricated from an x-ray absorbing material, for example, tungsten.

As a result of the eccentric shape, the rotation of respective cams 120A and 120B alters the z-axis profile of x-ray beam 16. More specifically, altering position of cams 120A and 120B alters the position and width of x-ray beam umbra. Particularly, as a result of the jointly stepping eccentric shape of cams 120A and 120B, the total width of x-ray beam umbra is altered. Altering the position, or stepping, cam 120A, alone, alters the umbra width and position relative to one edge of detector array 18. Altering the position of cam 120B, alone, alters the umbra width and position relative to the other, or second edge, of detector array 18 so that the x-ray dosage received by patient 22 is reduced.

Further details regarding a multislice scanning system are set forth in copending U.S. patent application Ser. No. 09/140,289, entitled Scaleable Multislice Imaging System, which is assigned to the present assignee and hereby incorporated herein, in its entirety, by reference.

In operation, x-ray source 14 is fixed, or placed in a stationary position, and respective cams 120A and 120B are placed in nominal positions so that an x-ray beam 16 is radiated through collimator 92 toward detector array 18. Projection data from the detector is reconstructed by computer 36 using a fan beam filtered backprojection algorithm. This algorithm uses a $1/R^2$ weighting factor where R is the distance from a point in the image to the x-ray source. When the scanner geometry is short, this weighting factor increases noise variation in the image. More particularly, the noise is increased away from the center of the image.

Also, and as explained above, a multislice scanner typically has a shorter geometry which increases image noise away from the center of the image compared to other known longer geometry scanners. More particularly, and as a result of the geometry change and the fan beam reconstruction in the multislice system, to reduce the concentric force on the x-ray tube, the x-ray tube to iso-center distance needs to be reduced. Consequently, the magnification factor for such scanner increases, the scaling factor used in the fan beam backprojection increases, and the noise in the reconstructed image also increases.

The noise behavior is location dependent, and therefore, channel dependent, and DAS gain dependent. Because of the short geometry, the noise is roughly the same at the iso-center and increases as a function of distance to the iso-center. The noise in the reconstructed image is the roughly weighted average of the channel. The noise in the channel is mainly contributed to by the noise inside the circle described by the trajectory. Therefore, a smoothing function that increases noise suppression away from the iso channel will produce a increase noise suppression. It can be expressed as:

$$H(\gamma, k) = f(\gamma, k, g) \otimes D(\gamma, k) \qquad (1)$$

where H is the resulting composite filter that replaces the matrix deconvolution kernel, D, and f is the channel and DAS gain dependent smoothing filter convolved with the matrix deconvolution kernel D to produce the new kernel H. Also, $\gamma$ is the channel, g is the gain dependent smooth filter, and k represents the detector row number. In one embodiment, the filter is defined by a sequence of values (d, 1-2d, d) where:

$$d = m(1 - \sin(\gamma)/\gamma),$$

The above described filter is channel and DAS gain dependent. In addition, such filter can also be dependent on many other factors that affect the system noise, such as the reconstruction algorithms (e.g., the filter may differ for axial versus helical scans, and the filter may differ for high resolution versus low resolution mode).

Although the filter described above is configured as channel dependent filter to equalize noise in the image, it will be apparent to those skilled in the art that such a filter could also be used to enhance radial spatial resolution as a function of distance from the center of the image. This is desirable in certain clinical applications (such as high resolution lung scanning) where high spatial resolution is required to a radius of 17 cm in the image. Without such a filter, the width of the x-ray tube focal distribution function degrades spatial resolution with distance from the center of the image. In one embodiment, a spatial resolution enhancing filter could be achieved by defining m with a negative magnification factor such as m=−2.5. It will be apparent to those skilled in the art that many other channel dependent filter definitions are possible.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for reconstructing an image in an imaging system, said method comprising the steps of:
   performing a scan to obtain data; and
   performing channel dependent filtering of data.

2. A method in accordance with claim 1 wherein performing filtering of the data is executed in accordance with:

$$H(\gamma, k) = f(\gamma, k, g) \otimes D(\gamma, k)$$

where H is a resulting composite filter, D is a deconvolution filter, f is a channel and gain dependent smoothing filter, $\gamma$ is a channel, g is a gain dependent smoothing filter, and k is a detector row number.

3. A method in accordance with claim 1 wherein performing filtering on the data comprises the step of applying an enhancing filter to the data.

4. A method in accordance with claim 1 wherein performing filtering on the data comprises the step of applying a smoothing filter to the data.

5. A method in accordance with claim 1 wherein filtering the data is performed in accordance with (d, 1-2d, d) where:

$$d = m(1 - \sin(\gamma)/\gamma).$$

6. A method in accordance with claim 1 wherein the imaging system is a single slice system.

7. A method in accordance with claim 1 wherein the imaging system is a multislice system.

8. A method in accordance with claim 1 wherein the imaging system includes a data acquisition system, and the filtering also is data acquisition system gain dependent.

9. An imaging system comprising an x-ray source and at least one detector module, said system further comprising a data acquisition system coupled to said detector, said system configured to:
   perform a scan to obtain data; and
   perform channel dependent filtering of data.

10. A system in accordance with claim 9 wherein to perform filtering of the data, said system is configured to filter the data in accordance with:

$$H(\gamma, k) = f(\gamma, k, g) \otimes D(\gamma, k)$$

where H is a resulting composite filter, D is a deconvolution filter, f is a channel and gain dependent smoothing filter, $\gamma$ is a channel, g is a gain dependent smoothing filter, and k is a detector row number.

11. A system in accordance with claim 9 wherein to perform filtering on the data, said system is configured to apply an enhancing filter to the data.

12. A system in accordance with claim 9 wherein to perform filtering on the data, said system is configured to apply a smoothing filter to the data.

13. A system in accordance with claim 9 wherein to filter the data, said system is configured to filter the data in accordance with (d, 1-2d, d) where:

$$d = m(1 - \sin(\gamma)/\gamma).$$

14. A system in accordance with claim 9 wherein said detector is a single slice detector.

15. A system in accordance with claim 9 wherein said detector is a multislice detector.

16. A system in accordance with claim 9 wherein said filtering also is data acquisition system gain dependent.

* * * * *